United States Patent [19]

Arnold

[11] Patent Number: 5,335,260
[45] Date of Patent: Aug. 2, 1994

[54] CALIBRATION PHANTOM AND IMPROVED METHOD OF QUANTIFYING CALCIUM AND BONE DENSITY USING SAME

[76] Inventor: Ben A. Arnold, 10r Public Sq., Columbia, Ky. 42728

[21] Appl. No.: 981,263

[22] Filed: Nov. 25, 1992

[51] Int. Cl.$^5$ .......................................... G01D 18/00
[52] U.S. Cl. .................................. 378/207; 378/18; 378/56
[58] Field of Search ................ 378/207, 204, 18, 162, 378/163, 165, 54, 56

[56] References Cited

U.S. PATENT DOCUMENTS

| | | | |
|---|---|---|---|
| 2,399,650 | 5/1946 | Moyer | 378/207 |
| 2,426,884 | 9/1947 | Kieffer | 378/207 |
| 4,115,691 | 9/1971 | Oldendorf . | |
| 4,115,762 | 9/1978 | Akiyama et al. . | |
| 4,124,799 | 11/1978 | Schittenhelm . | |
| 4,233,507 | 11/1980 | Volz . | |
| 4,400,827 | 8/1983 | Spears | 378/207 |
| 4,475,122 | 10/1984 | Green . | |
| 4,593,406 | 6/1986 | Stone . | |
| 4,649,561 | 3/1987 | Arnold . | |
| 4,724,110 | 2/1988 | Arnold . | |
| 4,811,373 | 3/1989 | Stein . | |
| 4,922,915 | 5/1990 | Arnold et al. . | |
| 4,941,164 | 7/1990 | Schuller et al. | 378/207 |
| 4,985,906 | 1/1991 | Arnold . | |
| 5,005,196 | 4/1991 | Lanza et al. | 378/207 |
| 5,122,664 | 6/1992 | Ito et al. | 378/207 |
| 5,187,731 | 2/1993 | Shimura | 378/207 |

OTHER PUBLICATIONS

Robert H. Heil, Jr., et al., "Quantitative Materials Evaluation and Inspection with the Imaging Analysing Computer", Proceedings of the Society of Photo-Optical Instrumentation Engineers, Feb. 1972, pp. 131-143.
K-P Hermann, et al., "Polyethylene-Based Water--Equivalent Phantom Material for X-Ray Dosimetry at Tube Voltages from 10 to 100 kV", Phys. Med. Biol., vol. 30, No. 11, 1985, pp. 1195-1200.
K-P Hermann, et al., "Muscle and Fat-Equivlent Polyethylene-Based Phantom Materials for X-Ray Dosimetry at Tube Voltages Below 100 kV", Phys. Med. Biol., vol. 31, No. 9, 1986, pp. 1041-1046.
Christopher E. Cann, et al., "Precise Measurement of Vertebral Mineral Content Using Computed Tomography", Journal of Computer Assisted Tomography, vol. 4, No. 4, Aug. 1980, pp. 493-500.
Christopher E. Cann, et al., "Low-Dose CT Scanning for Quantitative Spinal Mineral Analysis", Radiology, vol. 140, No. 3, Sep. 1981, pp. 813-815.
Robert G. Zamenhof, et al., "A Theoretical Sensitivity Evaluation of CT for the Measurement of Bone Mineral in Cortical and Vertebral Bone", Journal of Computer Assisted Tomography, Proceeding of CT Densitometry Workshop, vol. 3, No. 6, 1979, p. 852.
Technical Note, "Automatic Outlining Technique for EMI Scanner Pictures", Med. & Biol. Eng. & Comput., 17, Sep. 1979, pp. 693-694.
R. E. Baldy, et al., "A Fully-Automated Computer Assisted Method of CT Brain Scan Analysis for the

(List continued on next page.)

Primary Examiner—David P. Porta
Attorney, Agent, or Firm—Knobbe, Martens, Olson & Bear

[57] ABSTRACT

A calibration phantom representative of human tissue containing variable concentrations of calcium serves as a calibration reference for quantifying calcium, bone mass and bone mineral density in radiography and CT imaging systems. The method of fabrication of the calibration phantom provides the long-term stable incorporation of calcium into a tissue equivalent material which allows accurate, standardized, and reproducible quantification of calcium and bone mineral density in radiography and CT imaging systems. A method of using the calibration phantom for quantifying calcium and bone includes placement of part of a patient's anatomy in a bolusing apparatus to provide uniform attenuation of the x-ray beam passing through and around the patient's anatomy. A x-ray filter plate may be used to predictably attenuate the x-ray beam.

19 Claims, 4 Drawing Sheets

OTHER PUBLICATIONS

Measurement of Cerebrospinal FLuid Spaces and Brain Absorption Density", *Neuroradiology*, vol. 28, 1986, pp. 109–117.

James M. Keller, et al., "Automatic Outlining of Regions on CT Scans", *Journal of Computer Assisted Tomography*, vol. 5, No. 2, Apr. 1981, pp. 240–245.

W. A. Kalender, et al., "Methodological Aspects of Bone Mineral Measurements by QCT: Minimizing Operator Influence on Reproductibility," Proceedings of the Sixth International Workshop on Bone and Soft Tissue Densitometry, Buxton, England, Sep. 22–25, 1987, p. 31.

P. F. Wankling, et al., "Computer Recognition Applied to C.T. Scans for the Automation of the Procedure for Bone Mineral Measurement Allowing Consistent Measurement Without Operator Intervention", Proceedings of the Sixth International Workshop on Bone and Soft Tissue Densitometry, Buxton, England, Sep. 22–25, 1987, p. 32.

Willi A. Kalender, et al., "Vertebral Bone Mineral Analysis: An Integrated Approach with CT", *Radiology* 1987, vol. 164, No. 2, Aug. 1987, pp. 419–423.

J. L. Grashuis, et al., "Semi-Automatic Contour Detection in CT-Scans of the Lumbar Spine", Proceedings of the Sixth International Workshop on Bone and Soft Tissue Densitometry, Buxton, England, Sep. 22–25, 1987, p. 33, published in Calcified Tissue, vol. 44, No. 2, Feb. 198, p. 147.

Marketing materials from General Electric distributed in 1987 (four pages).

Christopher E. Cann, et al., "Spinal Mineral Loss in Oophorectomized Women", *JAMA*, No. 7, 1980, vol. 244, No. 18, pp. 2056–2059.

Heuck, "Quantitative Measurements of Mineral Content in Bone Disease," Session 10, Symposium Ossium E.S. Livingstone, Edingburgh, Scotland (1970), pp. 141–147.

Vogel, "Application Principles and Technical Considerations in SPA," in Proceedings Osteoperosis Update Harry Jerant ed., Radiology Research and Education Foundation, University of California printing (1987), pp. 219–231.

Felicia Cosman, et al., "Radiographic Absorptiometry: A Simple Method for Determination of Bone Mass", *Osteoporosis International*, 1991, pp. 34–38.

Copy of a brochure on "Bone Mineral Density Evaluation" by CompuMed.

S. Serpico, et al., "Evaluation and Standardization in Bone Densitometry", Transactions of the Fifth International Workshop on Bone and Soft Tissue Densitometry Using Computed Tomography, The University of Pennsylvania, Oct. 14–18, 1985.

M. E. Bolander, et al., "Quantitative Digital Subtraction Radiography: A Clinical Method for Bone Mineral Determination", Transactions of the Fifth International Workshop on Bone and Soft Tissue Densitometry Using Computed Tomography, The University of Pennsylvania, Oct. 14–18, 1985.

D. J. Hawkes, et al., "Development of a Digital Radiographic Technique to Measure Bone Mineral in Neonates", Transactions of the Fifth International Workshop on Bone and Soft Tissue Densitometry Using Computed Tomography, The University of Pennsylvania, Oct, 14–18, 1985.

Robert A. Kruger, Ph.D., et al., "Dual Energy Film Subtraction Technique for Detecting Calcification in Solitary Pulmonary Nodules", *Radiation Physics*, vol. 140, Jul. 1981, pp. 213–219.

X-RAYS

CALIBRATION PHANTOM AND IMPROVED METHOD OF QUANTIFYING CALCIUM AND BONE DENSITY USING SAME

BACKGROUND OF THE INVENTION

1. Field of the Invention

The present invention relates to a calibration device for radiography and X-ray computed tomography systems, and more specifically, to a calibration phantom which incorporates calcium into a human tissue equivalent material in terms of x-ray beam attenuation and scatter, and methods of fabrication and use of the same.

2. Description of the Related Art

Osteoporosis is the most common disorder of the human skeletal system, affecting up to 32 percent of women and 17 percent of men, depending upon the age group under consideration, Basically, osteoporosis is a disease process in which the mineral content (i.e., calcium content) of a person's skeletal system is gradually reduced, leading to a higher risk of fractures particularly in the spine, hip, and wrist. Osteoporosis is a major medical problem. It has been estimated that approximately 40,000 American women die per year from complications due to osteoporosis.

In the past, osteoporosis was considered to be undiagnosable prior to the onset of symptoms, and untreatable once it became symptomatic. Thus, it was frequently called the "silent disease." More recently, however, techniques have been developed which detect the early mineral loss in a person's bones. Such techniques include computed tomography (CT) quantitative computed tomography (QCT) and dual-energy x-ray absorptometry (DEXA).

Computed tomography uses an array of detectors to collect x-ray attenuation data from x-ray beams that pass through the body. The data are input as digital data to a computer, which processes that data and reconstructs planar cross-sectional images of the internal structures of the body through which the x-ray beams pass.

DEXA uses a dual energy approach to compensate for tissue variations to allow quantification of bone mass in a projection image. QCT requires the use of a bone-equivalent calibration phantom which is scanned simultaneously with the patient to provide bone density measurements in axial images.

Each of these methods require access to and use of sophisticated and relatively expensive equipment. In addition, the images produced can vary significantly in response to a number of technical factors related to the apparatus used, as well as errors caused by beam hardening and scattered radiation within the human body.

Plain film radiographs are frequently taken to qualitatively assess bone density throughout the body. Conventional radiographic apparatuses are widely available throughout the world and thus allow easy access for most patients. Although these radiographs provide very high spatial resolution and indicate relative attenuation of neighboring tissues, they are highly inaccurate and subject to gross misjudgment in assessing the patient's condition in terms of bone mass. Due to a variety of technical factors, quantification of calcium density from single energy projection radiography has not been possible.

In particular, quantitative x-ray measurements are influenced by x-ray beam hardening due to the broad spectral distribution of x-rays. As the x-rays pass through tissue or any other medium, lower energy x-rays are preferentially absorbed. This results in a shifting of the effective beam energy to higher values. Thus, the quantitative results which are obtained will vary with the size and shape and composition of the particular patient's anatomy.

The detection and quantification of calcification in pulmonary nodules, coronary arteries, aortic calcification, breast tumors and the like has been a goal of clinical radiology for some time. Cine CT, dual energy digital subtraction fluoroscopy, and dual energy film subtraction radiography have been tried. It has long been desirable, however, to quantify calcium or bone density in conventional x-ray projection images without using dual energy techniques.

Stepwedges using material of varying thickness are frequently used in radiology for quality control testing of x-ray beam properties. By varying the thickness of the steps, the intensity and spectral content of the x-ray beam in the projection image can be varied.

Stepwedges are commonly made of aluminum, copper and other convenient and homogeneous materials of known x-ray attenuation properties. Stepwedges using bone-like absorption materials have been used in quality control tests to evaluate the ability of dual energy imaging to quantify pulmonary nodules, see Kruger, et al., "Dual Energy Film Subtraction Technique for Detecting Calcification in Solitary Pulmonary Nodules," *Radiology*, Vol. 140, pages 213–219, July 1981. Previous efforts have used bone phantoms imaged separately from the patient to test the sensitivity of the technique for quantification. These stepwedge-like phantoms use calcium phosphate powder or calcium phosphate powder in molten paraffin. Since the phantoms use powder and/or paraffin, they lack packing consistence, long term stability, and the homogeneity of mixing, which are desirable characteristics of a phantom used repeatedly over long periods of time.

There is therefore a substantial need for an improved test phantom representative of human tissue containing calcium in a long-term stable format, and a low cost method of quantifying bone density and calcium content which is fast, accurate, reproducible and widely available.

SUMMARY OF THE INVENTION

The present invention utilizes an improved calibration phantom formed of a material which simulates the properties of human tissue and contains calcium in a stable configuration and a modified technique to provide improved accuracy and precision in the quantification of calcium, bone mass and bone density using conventional X-ray equipment.

One aspect of the present invention is an improved solid water composition which comprises stable, human soft tissue equivalent materials with respect to x-ray attenuation and absorption characteristics. This solid water composition contains calcium homogeneously blended throughout the matrix. The calcium is preferably calcium phosphate, or more preferably, calcium hydroxyapatite. The water equivalent matrix approximates soft tissue, so that the incorporated calcium more accurately simulates bone or calcium in the body.

A second aspect of the present invention is an improved calibration phantom which comprises the solid water composition containing calcium which is both stable over long time periods and is homogeneously blended. The calcium is so blended and incorporated into the tissue equivalent plastic compound that clumping and variation in concentrations of calcium throughout the material can be avoided.

The method of fabricating the phantom of the present invention comprises forming the phantom from a low density polyethylene, calcium carbonate, and heavy magnesium oxide, and adding the desired concentration of calcium phosphate or calcium hydroxyapatite. By varying the loading of the calcium compound in the water-equivalent plastic, phantoms of various concentrations and densities can readily be fabricated and stepwedges of varying sizes and thicknesses can be constructed. The length and width of the individual steps can be varied depending on the area of the patient's body to be measured and the detector system used. The concentration of calcium compound per unit volume of matrix material can be varied to effectively change the thickness of the total stepwedge phantom. Since bone and calcium deposits in the body are known to be composed mainly of calcium hydroxyapatite, the phantom provides a more accurate simulation of human bone for calibration purposes.

In accordance with another aspect of the present invention there is provided a method of quantifying calcium using a calibration phantom composed of the solid water and calcium composition. The method involves simultaneously imaging or scanning the calibration phantom and the patient for the purpose of quantifying the patient's bone mass. Under the method of the present invention, the calibration phantom is imaged or scanned simultaneously with the individual patient for every exam. By placing the calibration phantom in the x-ray beam with the patient, reference calibration samples are present to allow corrections and calibration of the absorption properties of calcium and bone. When the phantom is imaged or scanned simultaneously with each patient, the variation in x-ray beam energy and beam hardening are corrected since the phantom and the patient both see the same x-ray beam spectrum. Each patient, having a different size, thickness, muscle-to-fat ratio, and bone content, attenuate the beam differently and thus change the effective x-ray beam spectrum. It is necessary that the bone-equivalent calibration phantom be present in the same beam spectrum as the patient's bone to allow accurate calibration.

The calibration phantom materials and method of the present invention are suitable for use in both conventional radiography systems and computed tomography (CT) systems. In conventional radiography systems, a stepwedge phantom fabricated from a matrix containing a desired concentration of calcium in varying thicknesses is used. In CT systems, a single bone mineral density (BMD) phantom having varying concentrations of calcium is used. In addition, the stepwedge calibration phantom of the present invention can be configured to be small enough and thin enough to be placed inside the mouth, and the method of the present invention can be used to quantify bone mass using standard dental x-ray systems.

In accordance with yet another aspect of the present invention, there is provided an attenuation apparatus used to standardize the patient-phantom attenuating mass and shape. The apparatus contains a homogeneous tissue-like material positioned and contained within a bolusing structure. The structure is of a predetermined and fixed size and shape. The tissue-like material consists, for example, of beads, gel, or water. The material is placed inside a bag which is placed within a holding structure to fix the shape and thickness of the tissue-like material. The calibration phantom is also positioned inside the structure at a fixed and reproducible location. The patient's wrist, hand, or other part of the anatomy is placed inside structure. The lid of the structure is then closed, and the portion of the patient's anatomy within the structure is surrounded by the tissue-like material. This results in the production of a constant thickness of tissue-like material that is reproducible. By fixing the thickness, x-rays which pass through the patient and bolusing apparatus are similarly attenuated, thus standardizing X-ray beam hardening. Further, each and all patients are imaged on the same apparatus, or on identical apparatuses, such that a standard of reference can be developed which is independent of patient size and tissue properties.

In accordance with still another aspect of the present invention, an x-ray filter plate is located between the source of the x-ray beam and the surface of the apparatus. The filter preferentially absorbs and attenuates x-rays of known energies. By varying the filter thickness, the degree of filtering can be changed. The broad spectral distribution of the x-ray beam can be narrowed significantly by use of the filter. Beam hardening is reduced as the beam becomes more monoenergetic. The filter thickness and material is selected based upon patient anatomy and required x-ray intensity for a given x-ray detector, x-ray tube output, exposure time and the like.

The present invention provides several advantages in improving the accuracy and precision of calcium, bone mass and bone density measurements. The constant path length of x-ray attenuation produces consistent and predictable beam hardening since the phantom and patient are both now surrounded by tissue-like material. Edge effects due to the phantom being placed at the edge of the field or in air near the patient's anatomy are removed. Cross-hairs may be placed on the apparatus for centering within the x-ray field, such that positioning and localization are facilitated on initial and repeat exams.

The improved method of use of the stepwedge calibration phantom of the present invention is simple to apply low-cost and greatly improves the accuracy of calcium and bone quantification in radiography. It is useful in both single energy and dual energy imaging techniques and allows new applications such as dental bone densitometry using conventional x-ray equipment and dental x-ray film.

DETAILED DESCRIPTION OF THE INVENTION

Figures 1, 2, 3:
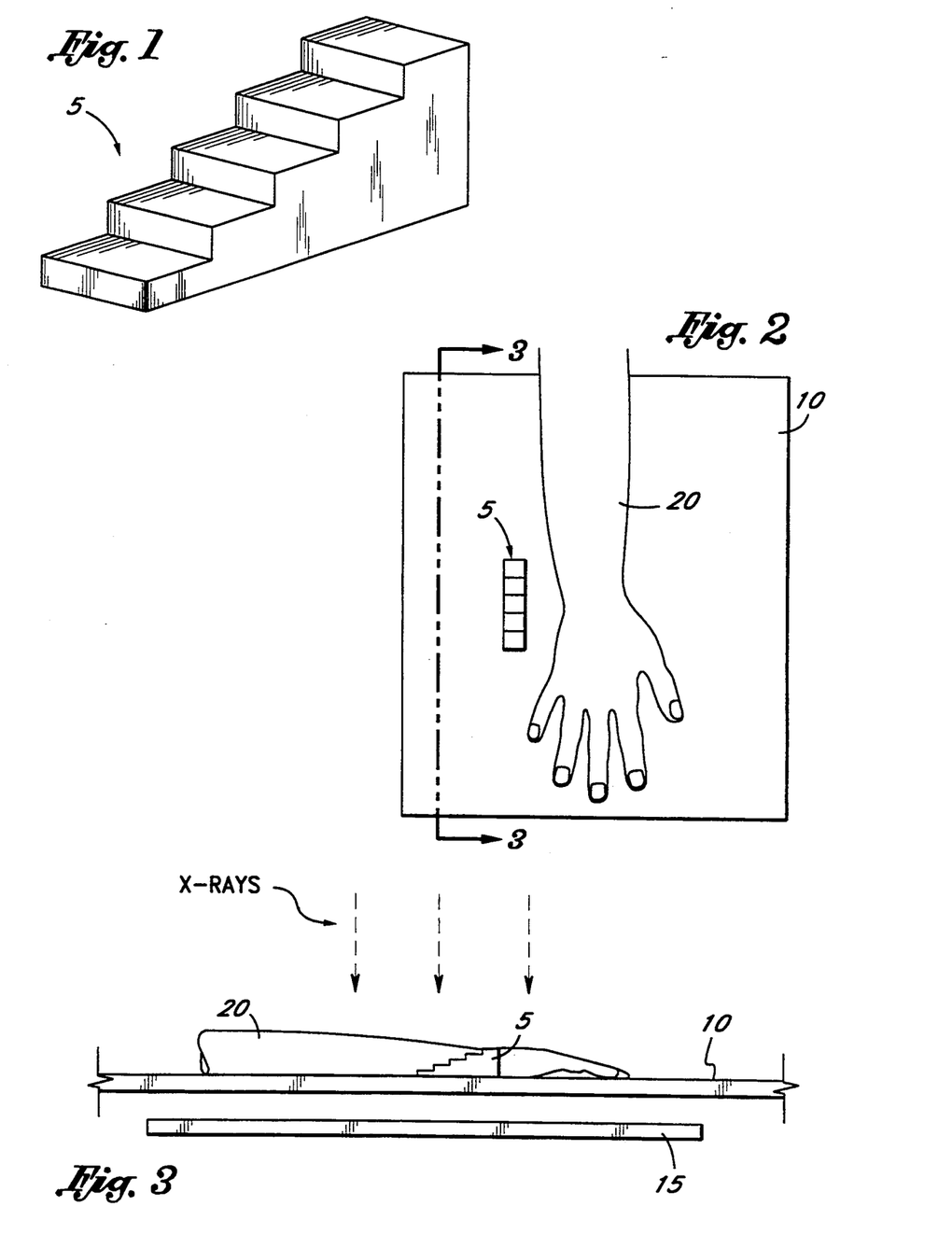
FIG. 1 is a perspective view of the stepwedge calibration phantom of the present invention.
FIG. 2 is a top view of the stepwedge calibration phantom of the present invention placed adjacent to the wrist of a patient prior to the simultaneous x-ray projection imaging of the patient's hand and wrist bones and the calibration phantom.
FIG. 3 is a side view taken along the line 3—3 in FIG. 2, showing simultaneous imaging of the calibration phantom and the patient's hand and wrist bones.

Referring to FIG. 1, there is shown the stepwedge calibration phantom 5 of the present invention. The stepwedge phantom 5 comprises a material which is substantially equivalent to human soft tissue in regard to x-ray absorption and attenuation properties, blended with a calcium compound, resulting in a calibration phantom having a known concentration of calcium. In the preferred embodiment shown in FIG. 1, the bone equivalent material is fabricated into a configuration having increasing step height. Those skilled in the art will recognize that other configurations can be utilized without departing from the spirit of the present invention.

Figure 9:
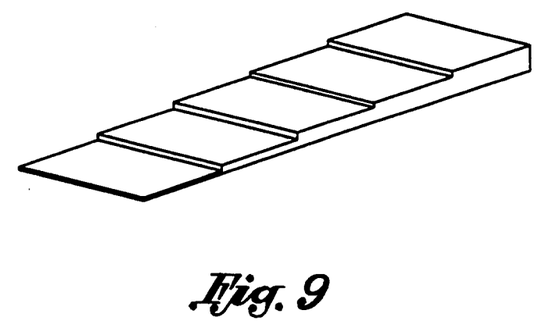
FIG. 9 is a perspective view of a second embodiment of the stepwedge calibration phantom of the present invention.

As illustrated in FIG. 9, the bone equivalent material is capable of being configured such that the resulting stepwedge is very thin. This allows new applications, such as the use of a stepwedge in dental x-rays, using conventional dental x-ray imaging systems.

The material utilized for the calibration phantoms of the present invention comprises a low atomic number material which is approximately tissue equivalent in regard to x-ray attenuation properties, which can be easily molded and fabricated into the desired geometries and which, in addition, is stable over prolonged periods of time. The preferred candidate is a proprietary mixture of material continuing linear low density polyethylene, combined with calcium carbonate and heavy magnesium oxide.

In a preferred embodiment, the tissue equivalent material is fabricated by combining 91.45% low density polyethylene (LDPE) (powder form, 0.928 g/cc specific gravity, melt index=2, Polymerland, Los Angeles, Calif.), 5.4% calcium carbonate (98% pure powder, UPS grade, 4 micron size, impurities known and listed, Pfizer, Los Angeles, Calif.), and 2.9% heavy magnesium oxide (white powder, 3.58 g/cc specific gravity, Vivion Chemical, Los Angeles, Calif.), all by weight. This material may additionally be advantageously dyed with 0.25% Ultra Marine Blue dye (0.25% by weight, PMS Consolidated, Los Angeles, Calif.), or other nonmetallic dyes well-known to those skilled in the art. To produce the calibration references, calcium is added to the tissue equivalent matrix. This calcium is preferably in the form of calcium phosphate or calcium hydroxyapatite (tribasic powder, Vivion Chemical, Los Angeles, Calif.). Material containing calcium in a concentration of 0.4 g/cc is used to fabricate the stepwedge calibration reference 5. To create the phantom used in CT systems, calcium is added to achieve final calcium concentrations of 0, 50, 100, and 200 mg/cc.

The materials are blended in powder form using a high intensity blender. The materials must be blended such that there is homogeneity and reproducibility on the order of about 0.2% within each sample and between samples. After blending, the mixture is extruded to pellets using a twin screw extruder. The resulting material is then compression molded into the desired configuration.

A method of using the stepwedge calibration phantom of the present invention to quantify bone mineral density using a conventional projection x-ray imaging system will now be explained with reference to FIGS. 2 and 3. As is well-known, the x-ray imaging system is composed generally of a high voltage generator x-ray tube (not shown), a tabletop or platform 10, and an x-ray imaging detector 15 which typically comprises a digital video detector, a solid state detector, or x-ray film. In operation, as illustrated in FIG. 2, the patient's hand and wrist 20 are placed flat on the x-ray table 10. The stepwedge phantom 5 is placed adjacent to the patient's wrist 20. As illustrated in FIG. 3, X-rays emanating from the x-ray tube (not shown) travel through the patient's hand and wrist 20 and the calibration phantom 5 simultaneously, and through the x-ray table 10 to impinge upon the x-ray imaging detector 15. The resultant image sensed by the detector 15 may then pass through an amplifier and a computer for processing, or may be recorded on x-ray film in a developer. The resulting image of the stepwedge phantom 5 is compared to the resulting image of the patient's hand and wrist bones. The patient's bone mass is then quantified, based on the density and thickness of the bone.

Figure 4:
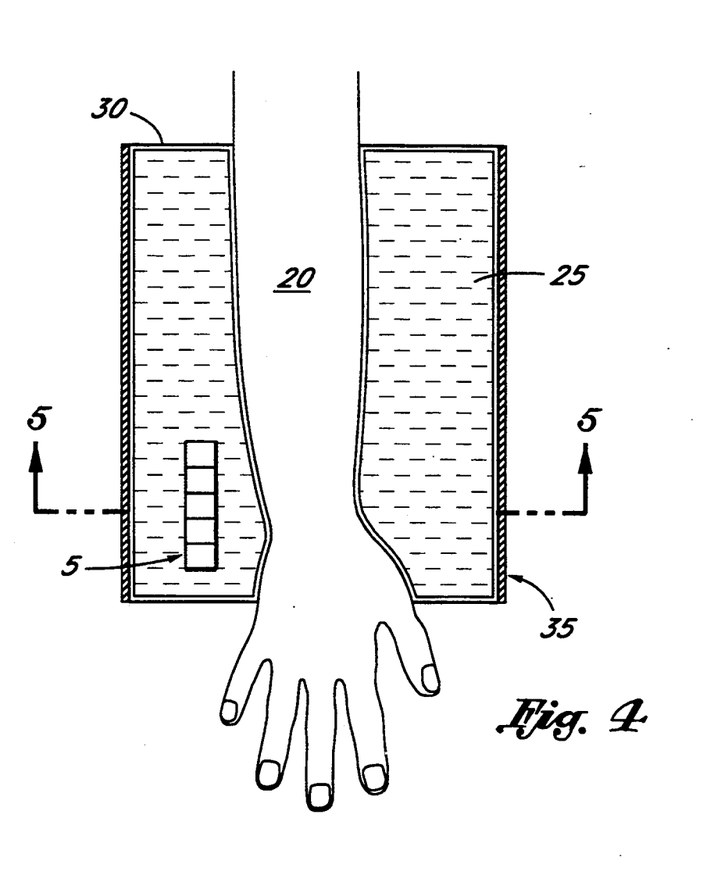
FIG. 4 is a cross-sectional top view of the attenuation apparatus of the present invention, showing the patient's hand and wrist inserted into the bolusing structure and the calibration phantom of the present invention placed adjacent to the patient's wrist for simultaneous x-ray imaging through the attenuation apparatus.
Figure 5:
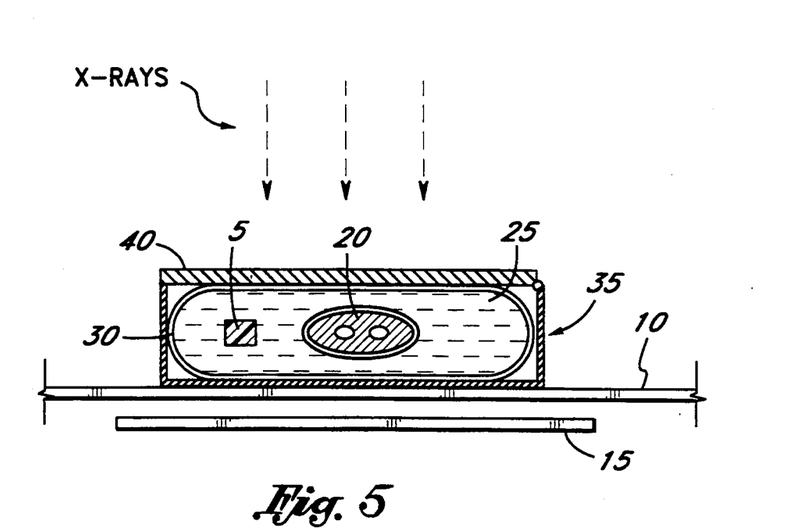
FIG. 5 is a cross-sectional side view taken along the line 5—5 in FIG. 4, showing the patient's arm and wrist bones adjacent to the calibration phantom surrounding by tissue equivalent material inside the attenuation apparatus of the present invention.

Referring now to FIGS. 4 and 5, there is shown a second embodiment of the present invention, which uses an attenuation apparatus 20 to standardize the patient-phantom x-ray beam attenuating mass and shape. The apparatus 20 contains a homogeneous tissue equivalent material 25 contained within a flexible bag 30 within a holding structure 35. The structure 35 is of a predetermined and fixed size and shape. The tissue-like material 25 consists, for example, of beads, gel, or water. The material 25 is placed inside a donut-shaped bag 30 which is placed within the holding structure 35 to fix the shape and thickness of the tissue-like material 25. The calibration phantom 5 is also positioned inside the structure at a fixed and reproducible location. The patient's wrist 20 is placed inside the center of the bag of tissue equivalent material 30 within the structure 35. The lid of the structure 40 is then closed, and the patient's wrist 20 and the calibration phantom 5 are surrounded by the tissue-like material 20. This results in the production of a constant thickness of tissue-like material that is reproducible. X-rays emanating from the x-ray tube (not shown) travel through the attenuation apparatus 35, through the patient's wrist 20 and the calibration phantom 5 simultaneously, and through the x-ray table 10 to impinge upon the x-ray imaging detector 15. The resultant image sensed by the detector 15 may then pass through an amplifier and a computer for processing, or may be recorded on x-ray film in a developer. The resulting image of the stepwedge phantom 5 is compared to the resulting image of the patient's wrist bones, and the patient's bone mass is quantified. By fixing the thickness of the tissue equivalent material 25 surrounding the patient's bones and the stepwedge calibration phantom 5, the x-rays are similarly attenuated, thus standardizing the beam hardening.

As illustrated in FIG. 5, an x-ray filter is used as the lid 40 of the attenuating apparatus 35. The quasi monoenergetic x-ray filter plate is located between the source of the x-ray beam (not shown) and the apparatus 35. The filter 40 preferentially absorbs and attenuates x-rays of known energies. By varying the filter thickness, the degree of filtering can be changed. The broad spectral distribution of the x-ray beam can be narrowed significantly by use of the filter 40. Beam hardening is reduced as the beam becomes more monoenergetic. The filter 40 is preferably made from copper, cerium, gadolinium, or other K-edge filters well known to those of skill in the art.

Figure 6:
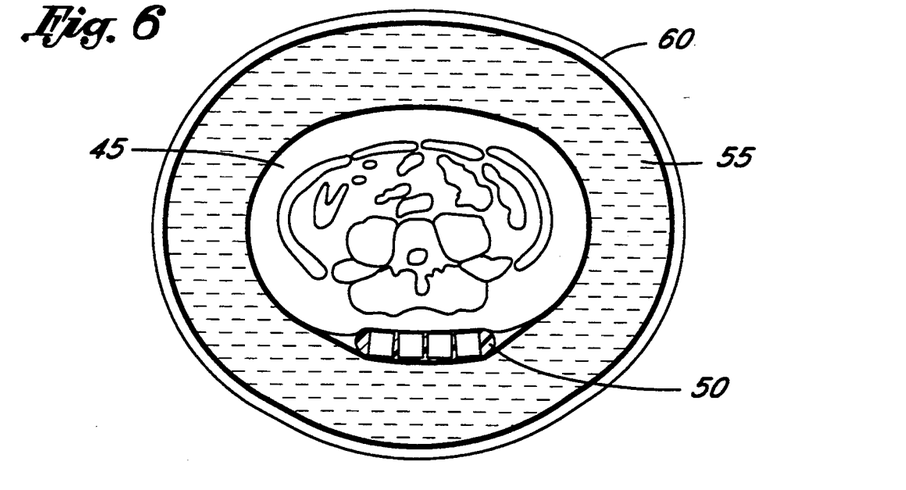
FIG. 6 is a diagrammatic representation of a typical transaxial tomographic slice provided by a CT scan, showing the calibration phantom of the present invention positioned beneath the patient's body, and the patient and phantom surrounded by tissue equivalent material and a quasi monoenergetic x-ray filter.

Referring now to FIG. 6, there is shown a reconstructed computed tomography image, showing the cross-section of the patient 45 and the bone mineral density (BMD) calibration phantom 50 surrounded by a tissue equivalent bolus 55, which is surrounded by a quasi monoenergetic x-ray filter 60. Generally, quantitative CT (QCT) bone densitometry is performed using a standard CT scanner. The patient lies on top of the BMD calibration phantom 50, which comprises samples of 0, 50, 100 and 200 mg/cc calcium hydroxyapatite in a tissue equivalent matrix. An x-ray source and collimator (not shown) project a thin fan-shaped beam of radiation which passes through the patient 45 and the BMD phantom 50 simultaneously, and which is then received by an x-ray detector (not shown). These signals are processed in a data acquisition system, and used by a computer to execute the image reconstruction algorithm. The resulting images of the patient 45 and the BMD calibration phantom 50 with its known calcium densities are compared to quantify the bone mineral density of the patient. The above-described computed tomography system is well known in the art.

Figure 7:
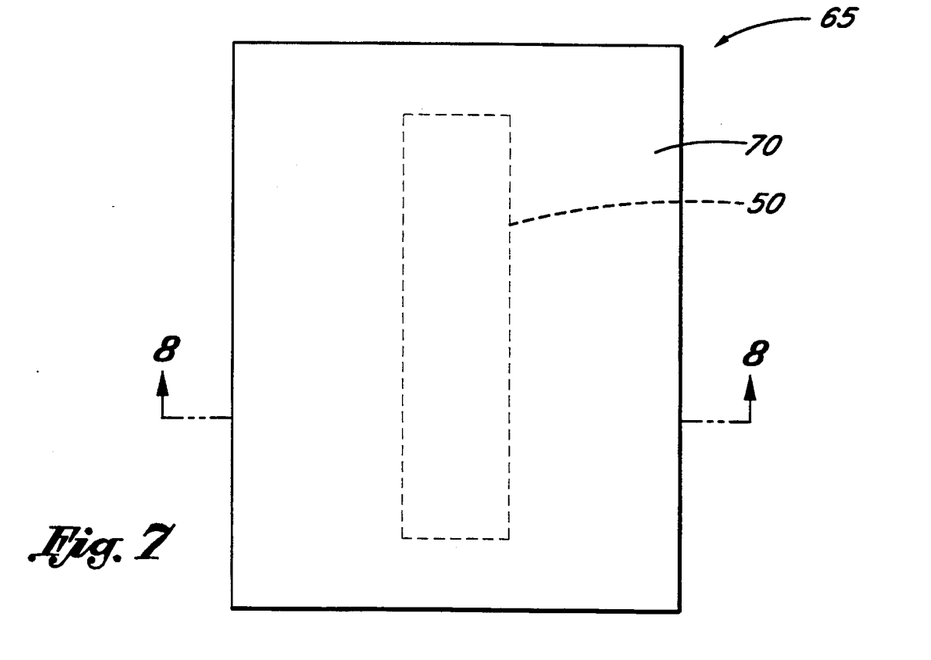
FIG. 7 is a top view of the CT couch pad of the present invention, showing the reference phantom positioned inside the pad.
Figure 8:
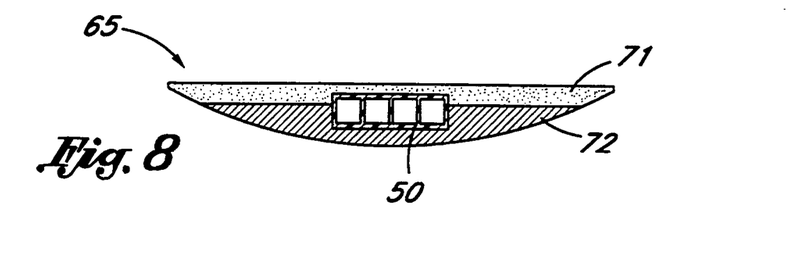
FIG. 8 is a cross-sectional view of the couch pad taken along the line 8—8 in FIG. 7.

Turning now to FIGS. 7 and 8, there is shown a couch pad 65 containing the BMD calibration phantom 50 of the present invention, suitable for use with QCT imaging systems. As shown in FIG. 7, the pad 65 contains a BMD calibration phantom 50 surrounded by tissue equivalent material 70. As illustrated in FIG. 8, the pad contains a top layer of a tissue equivalent gel 71, and a bottom portion which is filled with a thicker, firmer layer of the gel 72. As the patient lies on the pad 65, the pad 65 contours into the patient's spine, eliminating air space between the patient's body and the BMD calibration phantom 50. QCT bone densitometry is performed using a standard CT scanner. The patient lies on top of the pad 65 containing the BMD calibration phantom 50, which comprises samples of 0, 50, 100 and 200 mg/cc calcium hydroxyapatite in a tissue equivalent matrix. An x-ray source and collimator (not shown) project a thin fan-shaped beam of radiation which passes through the patient and the BMD phantom 50 simultaneously, and which is then received by an x-ray detector (not shown). These signals are processed in a data acquisition system, and used by a computer to execute the image reconstruction algorithm. The resulting images of the patient 45 and the BMD calibration phantom 50 with its known calcium densities are compared to quantify the bone mineral density of the patient.

Although for purposes of illustration certain materials, configurations, and sizes have been specified, those skilled in the art will recognize that various modifications can be made to the same without departing from the spirit of the present invention, and it is intended that the scope of this invention not be limited to the specific embodiments set forth herein. Accordingly, the scope of the invention is intended to be defined only by the claims which follow.

I claim:

1. A method of quantifying calcium and bone density in the body of a patient using a calibration reference phantom comprising stable, substantially human tissue equivalent material with respect to x-ray attenuation and absorption properties and calcium homogeneously blended therein, and an x-ray imaging system, comprising:

positioning the calibration phantom proximal to a part of the patient's anatomy such that x-rays pass through the patient and the phantom simultaneously;

placing said phantom and said portion of the patient's anatomy within an apparatus comprising a container having substantially human tissue equivalent materials with respect to x-ray attenuation and absorption characteristics in a bolusing structure of a fixed size and shape, such that the x-ray beam which passes through the patient and phantom is similarly attenuated and has a constant path length;

placing an x-ray filter plate between said apparatus and said x-ray beam to predictably attenuate the x-ray beam;

creating an image of the phantom and the portion of the patient's anatomy; and comparing the image of the phantom and the patient's anatomy to determine calcium content in the patient's anatomy.

2. The method of claim 1, wherein said calcium is calcium phosphate.

3. The method of claim 1, wherein said calcium is calcium hydroxyapatite.

4. The method of claim 1, wherein said tissue equivalent material comprises a mixture of low density polyethylene, calcium carbonate, and heavy magnesium oxide.

5. The method of claim 1 wherein said imaging system is a projection x-ray system and said calcium content is bone mass.

6. The method of claim 1 wherein said imaging system is a computed tomography system and said calcium content is bone density.

7. The method of claim 1, wherein said filter plate comprises a metal.

8. A method of quantifying bone density in a patient using a conventional dental x-ray system and a calibration reference phantom comprising stable, substantially tissue equivalent material with respect to x-ray attenuation properties and calcium homogeneously blended therein, comprising:

positioning the calibration reference phantom inside the patient's mouth such that x-rays pass through the patient and the phantom simultaneously, said calibration reference phantom being formed into varying effective thicknesses to simulate varying bone density;

creating an image of the phantom and the patient's bone using a single x-ray exposure; and comparing the image of the phantom and the patient's bone to determine bone density in the patient.

9. The method of claim 8, wherein said calcium is calcium phosphate.

10. The method of claim 8, wherein said calcium is a calcium hydroxyapatite.

11. A method of quantifying bone density in a patient using a conventional dental x-ray system and a calibration reference phantom comprising stable, substantially tissue equivalent material with respect to x-ray attenuation properties and calcium homogeneously blended therein, comprising:

positioning the calibration reference phantom inside the patient's mouth such that x-rays pass through the patient and the phantom simultaneously, said calibration reference phantom being formed into varying effective thicknesses to simulate varying bone density;

creating an image of the phantom and the patient's bone using a single x-ray exposure; and     comparing the image of the phantom and the patient'-bone to determine bone density in the patient,     wherein said tissue equivalent material comprises a mixture of polyethylene, calcium carbonate, and magnesium oxide.

12. A method of quantifying bone density in a living subject using a projection x-ray imaging system and a calibration reference phantom, comprising:

placing a phantom adjacent to a portion of the subject, said phantom having varying effective thicknesses of substantially tissue equivalent material with respect to x-ray attenuation properties, said substantially tissue equivalent material having calcium blended homogeneously therein so that said varying effective thicknesses of said phantom provide multiple calibrations;

creating an image of the phantom and the portion of the subject simultaneously using a single x-ray exposure and an imaging detector; and     comparing the images of the phantom and the portion of the subject to quantitatively determine bone density in the subject.

13. The method of claim 12, wherein said phantom is a stepwedge phantom.

14. The method of claim 12, wherein said imaging detector is x-ray film.

15. The method of claim 12, wherein said comparing is performed using a computer.

16. A calibration reference phantom for use in quantifying bone density using a projection x-ray imaging system comprising:

a stable, substantially tissue equivalent material with respect to x-ray attenuation properties and calcium blended homogeneously therein, said material formed into varying effective thicknesses to provide multiple calibrations.

17. The calibration reference phantom of claim 16, wherein said calcium is calcium hydroxyapatite.

18. The calibration reference phantom of claim 16, wherein said tissue equivalent material comprises a mixture of polyethylene, calcium carbonate, and magnesium oxide.

19. The calibration reference phantom of claim 16, wherein said phantom has a step wedge shape.

* * * * *